(12) United States Patent
Chen et al.

(10) Patent No.: US 11,879,862 B2
(45) Date of Patent: Jan. 23, 2024

(54) SENSOR FOR DETECTING GAS ANALYTE

(71) Applicant: Carrier Corporation, Palm Beach Gardens, FL (US)

(72) Inventors: Winston Yen-Yu Chen, West Lafayette, IN (US); Lia Antoaneta Stanciu, West Lafayette, IN (US); Alexander Wei, West Lafayette, IN (US); Aiganym Yermembetova, West Lafayette, IN (US)

(73) Assignee: Carrier Corporation, Palm Beach Gardens, FL (US)

( * ) Notice: Subject to any disclaimer, the term of this patent is extended or adjusted under 35 U.S.C. 154(b) by 315 days.

(21) Appl. No.: 17/118,083

(22) Filed: Dec. 10, 2020

(65) Prior Publication Data

US 2021/0333227 A1 Oct. 28, 2021

Related U.S. Application Data

(60) Provisional application No. 63/013,648, filed on Apr. 22, 2020.

(51) Int. Cl.
*G01N 27/12* (2006.01)
*G01N 33/00* (2006.01)

(52) U.S. Cl.
CPC ......... *G01N 27/12* (2013.01); *G01N 33/0047* (2013.01)

(58) Field of Classification Search
CPC .. G01N 27/12; G01N 33/0047; G01N 27/127; G01N 27/125
See application file for complete search history.

(56) References Cited

U.S. PATENT DOCUMENTS

2005/0072213 A1\* 4/2005 Besnard ............... G01N 27/127 73/31.06
2017/0088429 A1\* 3/2017 Shin ........................ C01B 21/06

OTHER PUBLICATIONS

Fu, Wangyang, et al. "Ultrasensitive Ethene Detector Based on a Graphene-Copper(i) Hybrid Material." Nano Letters, vol. 17, No. 12, 2017, pp. 7980-7988., https://doi.org/10.1021/acs.nanolett. 7b04466 (Year: 2017).\*
Patel, Denish V., et al. "Gold(I) Tris(Mercaptoimidazolyl)Borate Chemistry: Synthesis and Molecular Structure of the First Trinuclear TMR Complex of a Transition Metal." Inorganic Chemistry Communications, vol. 9, No. 7, 2006, pp. 748-750., https://doi.org/10. 1016/j.inoche.2006.04.023 (Year: 2006).\*

(Continued)

*Primary Examiner* — Lyle Alexander
*Assistant Examiner* — Ali Husain Faraz
(74) *Attorney, Agent, or Firm* — Patricia S. Whitehouse

(57) ABSTRACT

A sensor and a method of using the sensor are disclosed. The sensor includes a conductive region in electrical communication with two electrodes, the conductive region including a MXene material combined with a mercaptoimidazolyl metal-ligand complex, wherein the MXene has the formula $M_{n+1}X_n$ and M is at least one of a Group 3 transition metal, Group 4 transition metal, Group 5 transition metal, and Group 6 transition metal, X is carbon, nitrogen or a combination thereof, and n has a value of 1 to 3. The sensor can be used to detect volatile compounds that have a double or triple bond.

18 Claims, 1 Drawing Sheet

(56) References Cited

OTHER PUBLICATIONS

Alhabeb et al., "Guidelines for Synthesis and Processing of Two-Dimensional Titanium Carbide (Ti3C2Tx MXene)", Chemistry of Materials, 2017, 29, pp. 7633-7644.
Koh et al., "Enhanced Selectivity of MXene Gas Sensors through Metal Ion Intercalation: In Situ X-ray Diffraction Study", ACS Sens. 2019, 4, pp. 1365-1372.
Lee et al., "Room-Temperature, Highly Durable Ti3C2Tx MXene/Graphene Hybride Fiberts for NH3 Gas Sensing", Applied Materials & Interfaces, ACS Publications, Feb. 10, 2020, 9 pages.
Soomro et al., "A mini-review on MXenes as versatile substrate for advanced sensors", Chinese Chemical Letters, 2019, 9 pages.

* cited by examiner

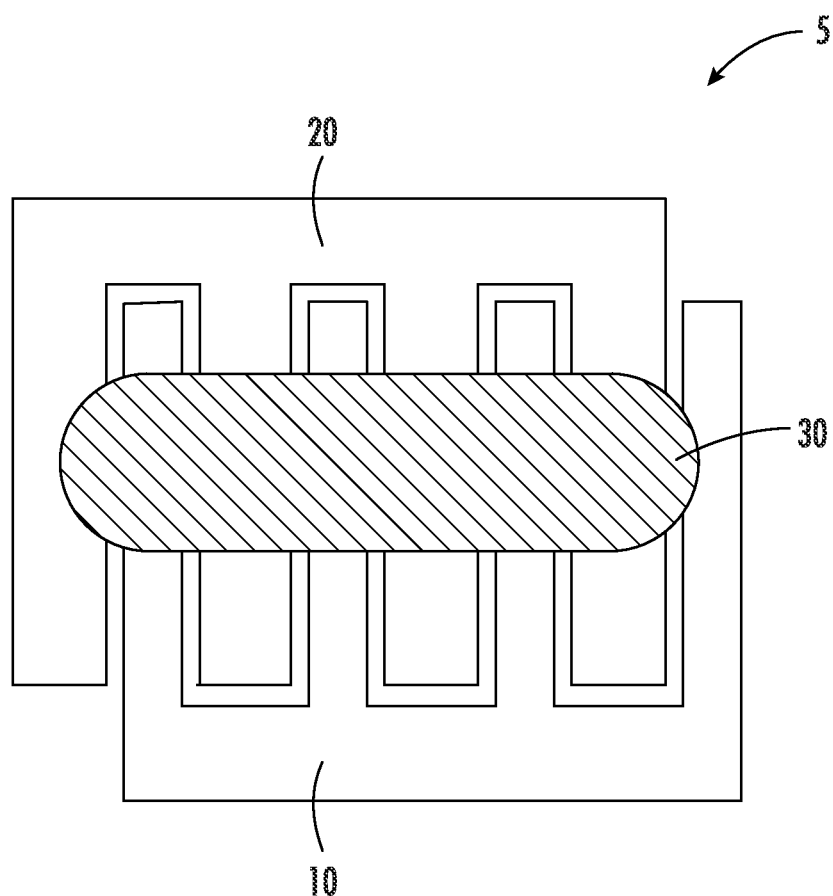

SENSOR FOR DETECTING GAS ANALYTE

CROSS-REFERENCE TO RELATED APPLICATIONS

This application claims the benefit of U.S. Provisional Application No. 63/013,648, filed Apr. 22, 2020, the disclosure of which is incorporated herein by reference in its entirety.

BACKGROUND

Exemplary embodiments pertain to the art of sensor compositions based on metal-ligand complexes.

Volatile compounds with a double bond form an important group of compounds for detection. In particular, volatile alkenes, such as ethylene, are analytes of considerable importance. In particular, the detection of ethylene is important to industries related to produce and agriculture. Due to its small size and limited chemical functionality, however, ethylene is a challenging chemical analyte to detect. More efficient and sensitive methods of detection than those currently available are desired.

BRIEF DESCRIPTION

Disclosed is a sensor including a conductive region in electrical communication with two electrodes, the conductive region including a MXene material combined with a mercaptoimidazolyl metal-ligand complex, wherein the MXene has the formula $M_{n+1}X_n$ and M is at least one of a Group 3 transition metal, Group 4 transition metal, Group 5 transition metal, and Group 6 transition metal, X is carbon, nitrogen or a combination thereof, and n has a value of 1 to 3.

In addition to one or more of the features described above, or as an alternative to any of the foregoing embodiments, the conductive region further includes a surfactant.

In addition to one or more of the features described above, or as an alternative to any of the foregoing embodiments, M includes Ti, V, Cr, Nb or a combination thereof.

In addition to one or more of the features described above, or as an alternative to any of the foregoing embodiments, the mercaptoimidazolyl metal-ligand complex includes more than one mercaptoimidazolyl group.

In addition to one or more of the features described above, or as an alternative to any of the foregoing embodiments, the mercaptoimidazolyl metal-ligand complex includes three mercaptoimidazolyl groups.

In addition to one or more of the features described above, or as an alternative to any of the foregoing embodiments, the mercaptoimidazolyl metal-ligand complex includes a pyrazolyl or indolyl group in addition to the mercaptoimidazolyl group(s).

In addition to one or more of the features described above, or as an alternative to any of the foregoing embodiments, the mercaptoimidazolyl metal-ligand complex includes Cu(I), Ag(I), or Au(I).

In addition to one or more of the features described above, or as an alternative to any of the foregoing embodiments, the mercaptoimidazolyl metal-ligand complex is a complex of formula (II):

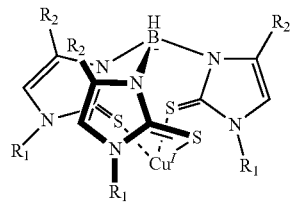

(II)

where each instance of $R_1$ and $R_2$ can be hydrogen or a group having one or more carbons.

Also disclosed is a method of sensing a volatile compound having a double or triple bond including exposing a sensor to a sample, the sensor including a conductive region in electrical communication with two electrodes, the conductive region including a MXene material combined with a mercaptoimidazolyl metal-ligand complex, wherein the MXene has the formula $M_{n+1}X_n$ and M is at least one of a Group 3 transition metal, Group 4 transition metal, Group 5 transition metal, and Group 6 transition metal, X is carbon, nitrogen or a combination thereof, and n has a value of 1 to 3, and measuring an electrical property at the electrodes.

In addition to one or more of the features described above, or as an alternative to any of the foregoing embodiments, the conductive region further includes a surfactant.

In addition to one or more of the features described above, or as an alternative to any of the foregoing embodiments, M includes Ti, V, Cr, Nb or a combination thereof.

In addition to one or more of the features described above, or as an alternative to any of the foregoing embodiments, the electrical property is conductivity.

In addition to one or more of the features described above, or as an alternative to any of the foregoing embodiments, the electrical property is resistivity.

In addition to one or more of the features described above, or as an alternative to any of the foregoing embodiments, the method further includes comparing an electrical property value obtained by measuring to a calibration curve to determine the quantity of a volatile compound having a double or triple bond present in the sample.

In addition to one or more of the features described above, or as an alternative to any of the foregoing embodiments, the volatile compound having a double or triple bond is ethylene.

In addition to one or more of the features described above, or as an alternative to any of the foregoing embodiments, the mercaptoimidazolyl metal-ligand complex includes more than one mercaptoimidazolyl group.

In addition to one or more of the features described above, or as an alternative to any of the foregoing embodiments, the mercaptoimidazolyl metal-ligand complex includes three mercaptoimidazolyl groups.

In addition to one or more of the features described above, or as an alternative to any of the foregoing embodiments, the mercaptoimidazolyl metal-ligand complex includes a pyrazolyl or indolyl group in addition to the mercaptoimidazolyl group(s).

In addition to one or more of the features described above, or as an alternative to any of the foregoing embodiments, the mercaptoimidazolyl metal-ligand complex includes Cu(I), Ag(I), or Au(I).

In addition to one or more of the features described above, or as an alternative to any of the foregoing embodiments, the mercaptoimidazolyl metal-ligand complex is a complex of formula (II):

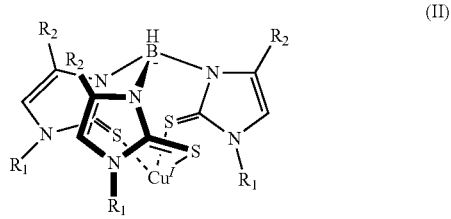

(II)

where each instance of $R_1$ and $R_2$ can be hydrogen, or a group having one or more carbons.

In another aspect, a method of preparing a sensor includes forming a conductive region including a MXene material combined with a mercaptoimidazolyl metal-ligand complex, wherein the MXene has the formula $M_{n+1}X_n$ and M is at least one of a Group 3 transition metal, Group 4 transition metal, Group 5 transition metal, and Group 6 transition metal, X is carbon, nitrogen or a combination thereof, and n has a value of 1 to 3 and placing the conductive region in electrical communication with two electrodes.

In addition to one or more of the features described above, or as an alternative to any of the foregoing embodiments, forming the conductive region includes depositing a MXene material in electrical communication with the two electrodes and depositing the mercaptoimidazolyl metal-ligand complex on the MXene material.

In addition to one or more of the features described above, or as an alternative to any of the foregoing embodiments, the electrodes are thin film electrodes.

BRIEF DESCRIPTION OF THE DRAWINGS

The following descriptions should not be considered limiting in any way. With reference to the accompanying drawings, like elements are numbered alike:

The FIGURE is a schematic of a sensor.

DETAILED DESCRIPTION

A detailed description of one or more embodiments of the disclosed apparatus and method are presented herein by way of exemplification and not limitation with reference to the FIGURE.

Volatile compounds with double or triple bonds are a group of important compounds for detecting and monitoring because of their significance to both the environment and, in the case of ethylene, for its role in produce ripening. The term volatile, as used herein, refers to compounds that are in the gas phase at standard temperature and pressure. Exemplary compounds include alkenes such as $C_2H_4$ (ethylene). As the hormone responsible for initiating the ripening of fruit as well as other processes in plant development, ethylene is an analyte of considerable importance to industries related to produce and agriculture. Due to its small size and limited chemical functionality, ethylene is a challenging chemical to detect. Disclosed herein is a sensor and a method that is capable of detecting volatile compounds with double bonds such as ethylene and other volatile alkenes at levels down to 100 parts per billion (ppb).

As shown in the FIGURE, the sensor 5 includes a conductive region 30 in electrical communication with at least two electrodes 10 and 20. The conductive region includes a MXene material combined with a mercaptoimidazolyl metal-ligand complex, wherein the MXene has the formula $M_{n+1}X_n$ and M is at least one of a Group 3 transition metal, Group 4 transition metal, Group 5 transition metal, and Group 6 transition metal, X is carbon, nitrogen or a combination thereof, and n has a value of 1 to 3. Exemplary transition metals M include titanium (Ti), vanadium (V), chromium (Cr), and niobium (Nb). The MXene may be doped or functionalized with a functional group. Exemplary functional groups include —OH, —$NH_2$, —COOH, sulfur and nitrogen.

MXenes are two dimensional materials synthesized from a MAX phase. MAX phases are layered ternary carbides and nitrides with the general formula $M_{n+1}AX_n$ where A is a Group 13 or Group 14 element. MXenes are generally synthesized from a MAX phase by wet chemical etching with hydrofluoric acid (HF) or an HF containing or HF forming etchant.

The MXene may be nanosized. "Nanosized" as it applies to MXene refers to the fact that the material has a thickness of less than or equal to 100 nanometers. The MXene may have a flake form with a thickness of 100 nanometers or less although other physical forms are not excluded such as few-layer or single-layer materials, with the caveat that the physical form has at least one linear dimension that is less than or equal to 100 nanometers.

The mercaptoimidazolyl metal-ligand complex is a multidentate coordination complex comprising one or more mercaptoimidazolyl groups. The arms of the multidentate ligand (groups on the boron atom) can be the same (homoleptic) or different (heteroleptic). For example, one arm can comprise a mercaptoimidazolyl group and a second arm can comprise a pyrazolyl or indolyl group. It is also contemplated that a multidentate ligand may comprise more than one mercaptoimidazolyl group or a combination of mercaptoimidazolyl group(s) and pyrazolyl group(s) or indolyl groups or both. The mercaptoimidazolyl metal-ligand complex may have formula (I)

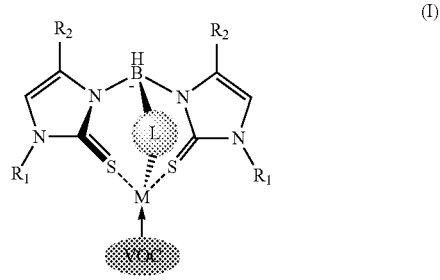

(I)

where each instance of $R_1$ and $R_2$ can be hydrogen or a group having one or more carbons. In some embodiments, each instance of $R_1$ and $R_2$ can be hydrogen or an alkyl group having 1 to 5 carbons. L in formula (I) can be a pyrazolyl group, a mercaptoimidazolyl group, or an indolyl. When L is a mercaptoimidazolyl group the multidentate metal-ligand complex can be described as homoleptic. When L is a group other than a mercaptoimidazolyl group the metal ligand complex can be described as a heteroleptic. VOC in formula I is present to show a postulated interaction with the volatile compound having a π bond. Without being bound by theory it is believed that the π bond of the volatile compound coordinates with an empty coordination site on the metal-ligand complex. The coordination alters the electronic configuration of the complex and can impact the electrical properties of the combination of the metal-ligand complex, nanosized particles of a metal dichalcogenide and metallic nanowires. In the case of a metal complex having formula II shown below, the resistivity of the combination of metal-ligand complex, nanosized particles of a metal dichalcogenide and metallic nanowires increases when the metal complex is bound to ethylene.

A more specific example of a mercaptoimidazolyl metal complex is shown in formula (II).

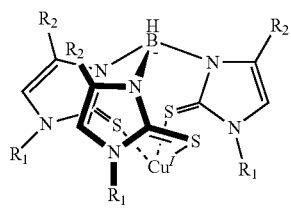

In formula (II) there are three mercaptoimidazolyl groups. $R_1$ and $R_2$ are defined as in formula (I).

The metal in the mercaptoimidazolyl metal complex may include Group 11 elements such as Cu(I), Ag(I), and Au(I).

The conductive region may further include a surfactant. Exemplary surfactants include dodecyltrimethylammonium bromide (DTAB), polyethylene glycol tert-octylphenyl ether (TRITON X-100), sodium deoxycholate, and combinations thereof.

The MXene is applied to a substrate. The substrate may be a flexible polymer film or other suitable material. Exemplary flexible polymer films include polyethylene terephthalate, polyethylene, polypropylene, polyamide, and polyvinyl chloride. The electrodes may be deposited on the substrate before the application of the MXene. The MXene may be applied by spray coating, dip coating, drop casting, or any other appropriate method. After the MXene is applied to the substrate the mercaptoimidazolyl metal-ligand complex is deposited on top of the MXene. The mercaptoimidazolyl metal-ligand complex may be applied by drop casting, dip coating, spray coating, or by electrospray. The layered material is then dried and is ready for use.

A method of sensing a volatile compound having a double or triple bond includes exposing a sensor as described above to a sample and measuring an electrical property at the electrodes. The electrical property can be conductivity or resistivity. The method can also include comparing the obtained electrical property value to a calibration curve to determine the quantity of the volatile compound present in the sample.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A sensor comprising a conductive region in electrical communication with two electrodes, the conductive region comprising a MXene material combined with a mercaptoimidazolyl metal-ligand complex, wherein the MXene has the formula $M_{n+1}X_n$, and M is at least one of a Group 3 transition metal, Group 4 transition metal, Group 5 transition metal, and Group 6 transition metal, X is carbon, nitrogen or a combination thereof, and n has a value of 1 to 3 and further wherein the mercaptoimidazolyl metal-ligand complex comprises heteroleptic ligand with a pyrazolyl or indolyl group in addition to the mercaptoimidazolyl group.

2. The sensor of claim 1, wherein the conductive region further includes a surfactant.

3. The sensor of claim 1, wherein M comprises Ti, V, Cr, Nb or a combination thereof.

4. The sensor of claim 1, wherein the mercaptoimidazolyl metal-ligand complex comprises a homoleptic ligand with three mercaptoimidazolyl groups.

5. The sensor of claim 1, wherein the mercaptoimidazolyl metal-ligand complex comprises Cu(I), Ag(I), or Au(I).

6. The sensor of claim 1, wherein the mercaptoimidazolyl metal-ligand complex is a homoleptic complex of formula (II):

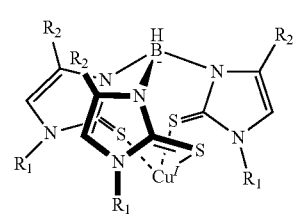

where each instance of $R_1$ and $R_2$ can be hydrogen, or a group having one or more carbons.

7. A method of sensing a volatile compound having a double or triple bond comprising exposing a sensor to a sample, the sensor comprising a conductive region in electrical communication with two electrodes, the conductive region comprising a MXene material combined with a mercaptoimidazolyl metal-ligand complex comprising a pyrazolyl or indolyl group in addition to the mercaptoimidazolyl group, wherein the MXene has the formula $M_{n+1}X_n$, and M is at least one of a Group 3 transition metal, Group 4 transition metal, Group 5 transition metal, and Group 6 transition metal, X is carbon, nitrogen or a combination thereof, and n has a value of 1 to 3, and measuring an electrical property at the electrodes.

8. The method of claim 7, wherein the conductive region further comprises a surfactant.

9. The method of claim 7, wherein M comprises Ti, V, Cr, Nb or a combination thereof.

10. The method of claim 7, wherein the electrical property is conductivity.

11. The method of claim 7, wherein the electrical property is resistivity.

12. The method of claim 7, further comprising comparing an electrical property value obtained by measuring to a calibration curve to determine the quantity of a volatile compound having a double or triple bond present in the sample.

13. The method of claim 12, wherein the volatile compound having a double or triple bond is ethylene.

14. The method of claim 7, wherein the mercaptoimidazolyl metal-ligand complex comprises three mercaptoimidazolyl groups.

15. The method of claim 7, wherein the mercaptoimidazolyl metal-ligand complex comprises Cu(I), Ag(I), or Au(I).

16. The method of claim 7, wherein the mercaptoimidazolyl metal-ligand complex is a complex of formula (II):

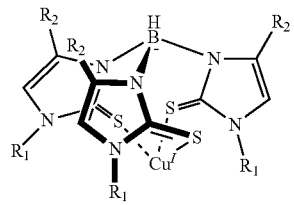

(II)

where each instance of $R_1$ and $R_2$ can be hydrogen, or a group having one or more carbons.

17. A method of preparing a sensor comprising forming a conductive region comprising a MXene material combined with a mercaptoimidazolyl metal-ligand complex comprising a pyrazolyl or indolyl group in addition to the mercaptoimidazolyl group, wherein the MXene has the formula $M_{n+1}X_n$, and M is at least one of a Group 3 transition metal, Group 4 transition metal, Group 5 transition metal, and Group 6 transition metal, X is carbon, nitrogen or a combination thereof, and n has a value of 1 to 3 and placing the conductive region in electrical communication with two electrodes.

18. The method of claim 17, wherein forming the conductive region comprises depositing a MXene material in electrical communication with the two electrodes and depositing the mercaptoimidazolyl metal-ligand complex on the MXene material.

\* \* \* \* \*